US012602777B2

(12) United States Patent
Lee et al.

(10) Patent No.: US 12,602,777 B2
(45) Date of Patent: Apr. 14, 2026

(54) APPARATUS AND METHOD FOR QUANTITATIVE ASSESSMENT OF MEDICAL IMAGES FOR DIAGNOSIS OF CHRONIC OBSTRUCTIVE PULMONARY DISEASE

(71) Applicants:CORELINE SOFT CO,, LTD., Seoul (KR); The Asan Foundation, Seoul (KR); UNIVERSITY OF ULSAN FOUNDATION FOR INDUSTRY COOP, Ulsan (KR)

(72) Inventors: Sang Min Lee, Seoul (KR); Joon Beom Seo, Seoul (KR); Jaeyoun Yi, Seoul (KR); Donghoon Yu, Gimpo-si (KR); Hye Jeon Hwang, Seoul (KR); Heejun Park, Gimpo-si (KR)

(73) Assignees: CORELINE SOFT CO., LTD., Seoul (KR); THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 447 days.

(21) Appl. No.: 18/123,853

(22) Filed: Mar. 20, 2023

(65) Prior Publication Data
US 2023/0342923 A1     Oct. 26, 2023

(30) Foreign Application Priority Data
Mar. 18, 2022     (KR) ........................ 10-2022-0034253

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/194* (2017.01); *G06T 7/70* (2017.01);
(Continued)

(58) Field of Classification Search
None
See application file for complete search history.

(56) References Cited

U.S. PATENT DOCUMENTS

| | | |
|---|---|---|
| 2007/0086636 A1 | 4/2007 | Keall et al. |
| 2013/0004044 A1* | 1/2013 | Ross .................... G06T 7/0016 382/128 |

FOREIGN PATENT DOCUMENTS

| | | |
|---|---|---|
| JP | 2016-193191 A | 11/2016 |
| WO | 2013/003826 A1 | 1/2013 |

OTHER PUBLICATIONS

Hwang HJ, Seo JB, Lee SM, Kim N, Yi J, Lee JS, Lee SW, Oh YM, Lee SD. New Method for Combined Quantitative Assessment of Air-Trapping and Emphysema on Chest Computed Tomography in Chronic Obstructive Pulmonary Disease: Comparison with Parametric Response Mapping. Korean J Radiol. Oct. 2021. (Year: 2021).*

(Continued)

*Primary Examiner* — SJ Park
*Assistant Examiner* — Caroline E. Depalma
(74) *Attorney, Agent, or Firm* — United One Law Group LLC; Kongsik Kim; Jhongwoo Peck

(57) ABSTRACT

Disclosed are a visualization method for assisting medical image diagnosis comprising: acquiring first intensity values of first voxels in a lung region during inspiration, segmented from a chest computed tomography (CT) image acquired during inspiration, as first coordinate values of the first voxels; acquiring differences between second intensity val-
(Continued)

ues of second voxels, registered into the first voxels as voxels in the lung region during expiration segmented from a chest CT image acquired during expiration, and the first intensity values as second coordinate values of the first voxels; and visualizing a distribution of the first voxels by mapping the first voxels based on the first coordinate values and the second coordinate values.

20 Claims, 22 Drawing Sheets

(51) Int. Cl.
| | |
|---|---|
| *G06T 7/194* | (2017.01) |
| *G06T 7/30* | (2017.01) |
| *G06T 7/70* | (2017.01) |
| *G16H 30/40* | (2018.01) |

(52) U.S. Cl.
CPC ............... *G16H 30/40* (2018.01); *G06T 7/30* (2017.01); *G06T 2207/10081* (2013.01); *G06T 2207/20021* (2013.01); *G06T 2207/30061* (2013.01)

(56) References Cited

OTHER PUBLICATIONS

Galbán et al., "CT-based Biomarker Provides Unique Signature for Diagnosis of COPD Phenotypes and Disease Progression," Nat Med., Nov. 2012, 18(11), 1711-1715.
Cho et al., "Quantitative CT Imaging in Chronic Obstructive Pulmonary Disease: Review of Current Status and Future Challenges", J Korean Soc Radiol 2018, 78(1), 1-12.

* cited by examiner

S200

Acquire first coordinate based on first intensity of first voxel in lung region inspiration image — S220

Acquire second coordinate based on difference of first intensity and second intensity of second voxel in lung region in expiration image — S240

Visualize distribution of first voxel by mapping first voxel based on first coordinate and second coordinate — S260

FIG. 3

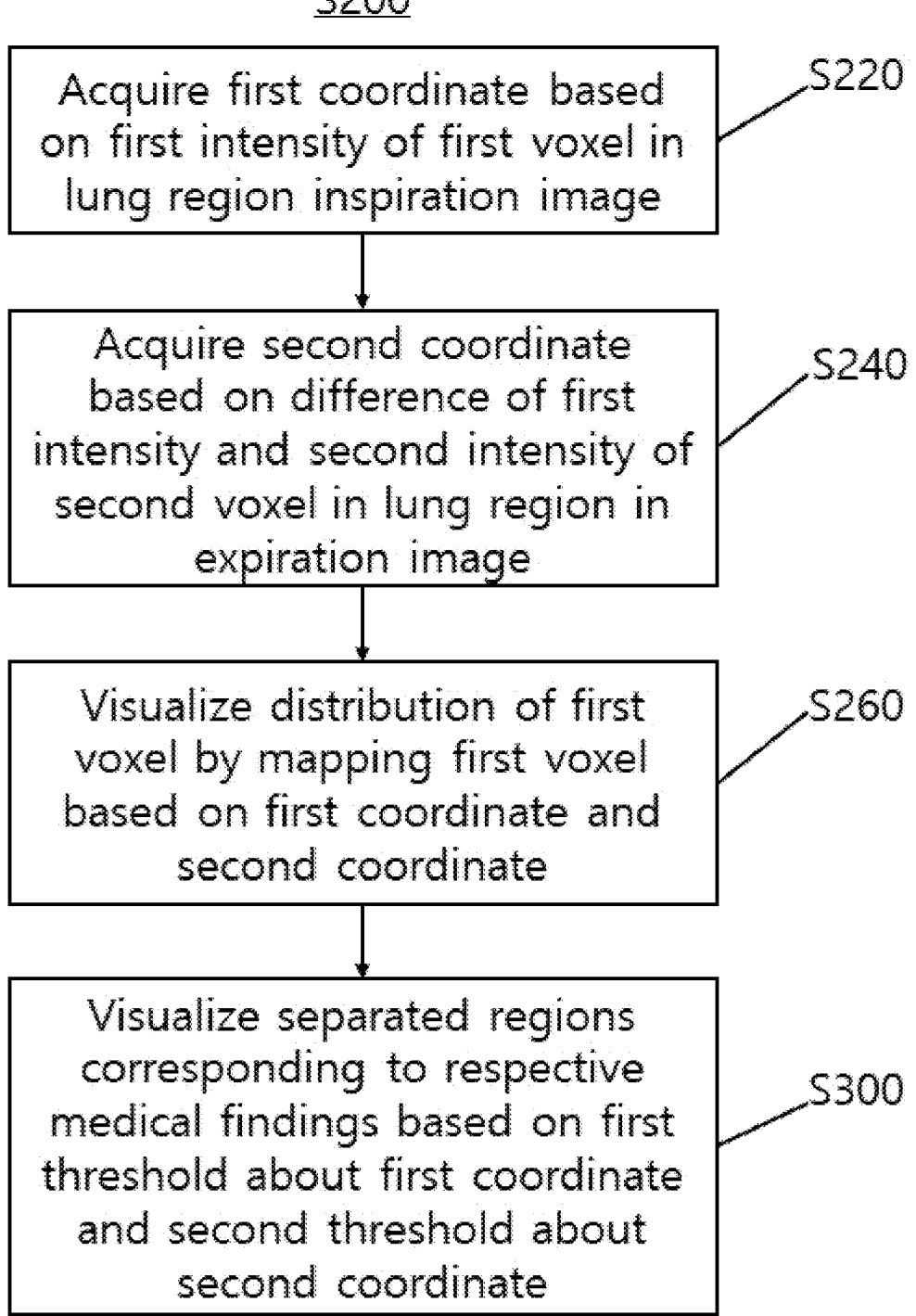

S200

Acquire first coordinate based on first intensity of first voxel in lung region inspiration image ___ S220

Acquire second coordinate based on difference of first intensity and second intensity of second voxel in lung region in expiration image ___ S240

Visualize distribution of first voxel by mapping first voxel based on first coordinate and second coordinate ___ S260

Visualize separated regions corresponding to respective medical findings based on first threshold about first coordinate and second threshold about second coordinate ___ S300

S300

(510)　(520)　(530)　(540)　(550)

APPARATUS AND METHOD FOR QUANTITATIVE ASSESSMENT OF MEDICAL IMAGES FOR DIAGNOSIS OF CHRONIC OBSTRUCTIVE PULMONARY DISEASE

CROSS-REFERENCE TO RELATED APPLICATIONS

The present application claims priority from Korean Application No. 10-2022-0034253, filed on Mar. 18, 2022, which is incorporated herein by reference in its entirety.

BACKGROUND

1. Technical Field

The present invention relates to technology for processing, analyzing, and visualizing medical images, and more particularly to technology for determining classification conditions for the quantitative assessment of medical images in accordance with clinical diagnostic purposes in order to assist in the diagnosis of chronic obstructive pulmonary disease (COPD).

2. Related Art

The contents described in this section merely provide information about the background art of the present invention and do not constitute prior art.

Various efforts have been made to extract useful information for clinical diagnosis from medical images.

In U.S. Patent Application Publication No. 2013/0004044 entitled "Tissue Phasic Classification Mapping System and Method," etc., attempts have been made to determine whether voxels in the lung region are dysfunctional and the type of functional failure based on the computed tomography (CT) intensity values of an expiratory image and the CT intensity values of an inspiratory image by using the expiratory and inspiratory images of the lung region.

However, the prior art has a need for improvement in clinical usefulness because the correlation between the results of the prior art and the results of clinical pulmonary function testing (PFT) is not yet high.

Therefore, there is a demand for a means for the quantitative assessment and visualization of lung function that can provide diagnostic assistance information that is designed to be more appropriate for clinical purposes and is intuitive.

SUMMARY

The present invention has been conceived to overcome the problems of the prior art, and an object of the present invention is to provide novel criteria for the quantitative assessment of the severity of a patient in order to diagnose COPD and to visualize and show the results of the quantitative assessment.

An object of the present invention is to, particularly, prevent a normal region from being unnecessarily classified as a disease region, and acquire accurate quantification indices by effectively identifying emphysema, an fAT region, and a normal region.

An object of the present invention is to acquire quantification indices significantly closer to the results of clinical PFT by acknowledging the presence of a functionally overlapping region without unduly classifying the region as an emphysema region or an fAT region.

According to an aspect of the present invention, there is provided a visualization method for assisting medical image diagnosis, the visualization method comprising: acquiring first intensity values of first voxels in a lung region during inspiration, segmented from a chest computed tomography (CT) image acquired during inspiration, as first coordinate values of the first voxels; acquiring differences between second intensity values of second voxels, registered into the first voxels as voxels in the lung region during expiration segmented from a chest CT image acquired during expiration, and the first intensity values as second coordinate values of the first voxels; and visualizing a distribution of the first voxels by mapping the first voxels based on the first coordinate values and the second coordinate values.

The visualization method may further comprise classifying and visualizing a plurality of regions corresponding to different medical findings based on a first threshold value for the first coordinate values and a second threshold value for the second coordinate values.

The visualization method may further comprise providing quantitative analysis results of a distribution of the first voxels in each of the plurality of regions as quantitative assessment information associated with a medical finding corresponding to each of the plurality of regions.

The visualization method may further comprise classifying and visualizing a region, in which the first coordinate values are smaller than a first threshold value and the second coordinate values are smaller than the second threshold value, as a functional air trapping (fAT) region.

The visualization method may further comprise classifying and visualizing a region, in which the first coordinate values are smaller than a third threshold value, as an emphysema region.

The visualization method may further comprise visualizing a region, belonging to both the fAT region and the emphysema region, using a visual element that can distinguish this region from remaining regions.

The visualization method may further comprise classifying and visualizing a region, in which the second coordinate values are smaller than the second threshold value and the first coordinate values are equal to or larger than the first threshold value, as a normal region.

The visualization method may further comprise classifying and visualizing a region, in which the second coordinate values are equal to or larger than the second threshold value and the first coordinate values are equal to or larger than the third threshold value, as a normal region.

The visualization method may further comprise segmenting the lung region during inspiration into a plurality of sub-regions, wherein the acquiring the first intensity values, the acquiring the differences, and the visualizing may be performed on at least one of the plurality of sub-regions.

The visualization method may further comprise further comprising segmenting the lung region during inspiration into a plurality of sub-regions, wherein the classifying and visualizing may be performed on at least one of the plurality of sub-regions.

According to an aspect of the present invention, there is provided a visualization apparatus for assisting medical image diagnosis, the visualization apparatus comprising: memory configured to store at least one instruction; and a processor configured to execute the at least one instruction, wherein the processor executes the at least one instruction to: acquire first intensity values of first voxels in a lung region during inspiration, segmented from a chest computed tomography (CT) image acquired during inspiration, as first coordinate values of the first voxels; acquire differences between second intensity values of second voxels, registered into the first voxels as voxels in the lung region during expiration segmented from a chest CT image acquired during expiration, and the first intensity values as second coordinate values of the first voxels; and visualize a distribution of the first voxels by mapping the first voxels based on the first coordinate values and the second coordinate values.

The processor may execute the at least one instruction to classify and visualize a plurality of regions corresponding to different medical findings based on a first threshold value for the first coordinate values and a second threshold value for the second coordinate values.

The processor may execute the at least one instruction to provide quantitative analysis results of a distribution of the first voxels in each of the plurality of regions as quantitative assessment information associated with a medical finding corresponding to each of the plurality of regions.

The processor may execute the at least one instruction to classify and visualize a region, in which the first coordinate values are smaller than a first threshold value and the second coordinate values are smaller than a second threshold value, as a functional air trapping (fAT) region.

The processor may execute the at least one instruction to classify and visualize a region, in which the first coordinate values are smaller than a third threshold value, as an emphysema region.

The processor may execute the at least one instruction to visualize a region, belonging to both the fAT region and the emphysema region, using a visual element that can distinguish this region from remaining regions.

The processor may execute the at least one instruction to classify and visualize a region, in which the second coordinate values are smaller than the second threshold value and the first coordinate values are equal to or larger than the first threshold value, as a normal region.

The processor may execute the at least one instruction to classify and visualize a region, in which the second coordinate values are equal to or larger than the second threshold value and the first coordinate values are equal to or larger than the third threshold value, as a normal region.

The processor may execute the at least one instruction to: segment the lung region during inspiration into a plurality of sub-regions; acquire the first intensity values as first coordinate values of the first voxels for at least one of the plurality of sub-regions; acquire differences between second intensity values of second voxels and the first intensity values as second coordinate values of the first voxels for at least one of the plurality of sub-regions; and visualize a distribution of the first voxels for at least one of the plurality of sub-regions.

The processor may execute the at least one instruction to: segment the lung region during inspiration into a plurality of sub-regions; and classify and visualize a plurality of regions corresponding to different medical findings for at least one of the plurality of sub-regions.

BRIEF DESCRIPTION OF THE DRAWINGS

The above and other objects, features and advantages of the present invention will be more clearly understood from the following detailed description taken in conjunction with the accompanying drawings, in which:

FIG. 3 is an operational flowchart showing in detail part S200 of a visualization method for assisting medical image diagnosis according to an embodiment of the present invention;

5

6

Figure 14:
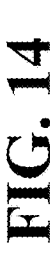
FIG. 14 is a conceptual view showing visualization results for assisting medical image diagnosis for the overall lung region according to still another embodiment of the present invention.
Figure 16:
FIG. 16 is a conceptual view showing visualization results for assisting in medical image diagnosis for the left lung region corresponding to FIG. 14.
Figure 20:
Figure 21:
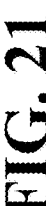
Figure 22:
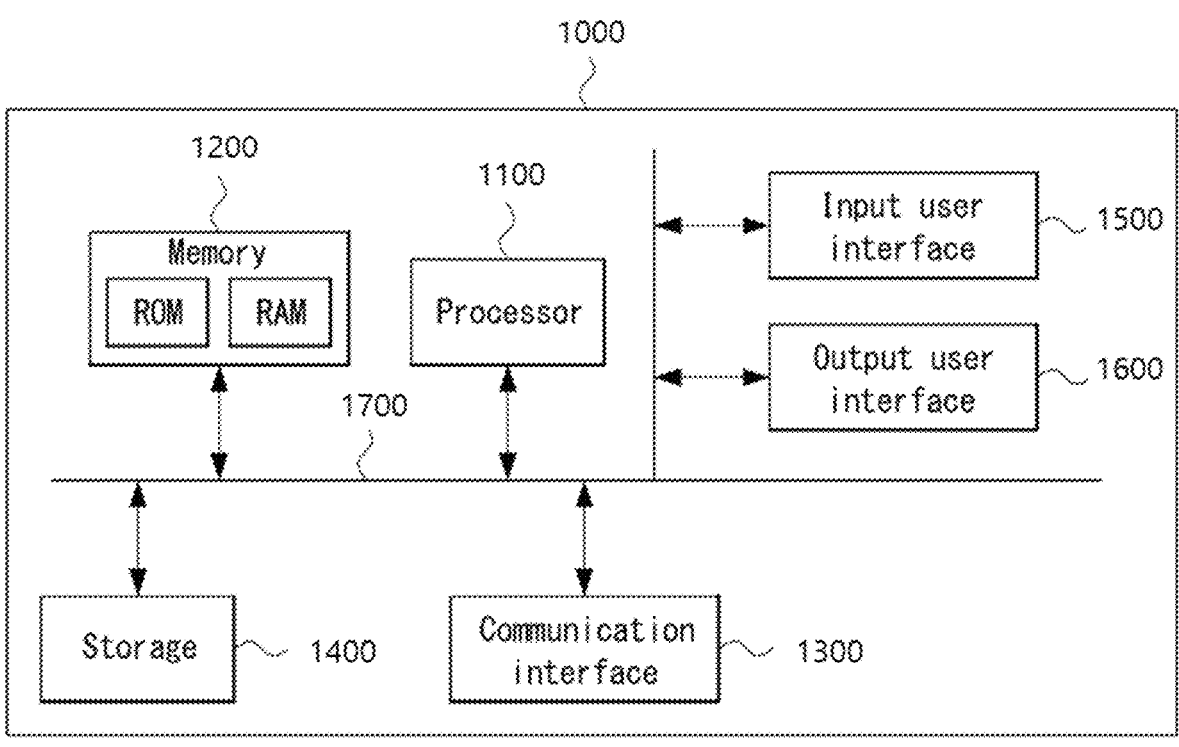

FIG. 20 is a conceptual view showing visualization results for assisting medical image diagnosis for the left upper lobe (LUL) region corresponding to FIGS. 14 and 16;

FIG. 21 is a conceptual view showing visualization results for assisting medical image diagnosis for the left lower lobe (LLL) region corresponding to FIGS. 14 and 16; and FIG. 22 is a conceptual diagram showing an example of a generalized medical image analysis apparatus, a visualization apparatus for assisting medical image diagnosis, or a computing system capable of performing at least part of the processes of FIGS. 1 to 21.

DETAILED DESCRIPTION

Since the present disclosure may be variously modified and have several forms, specific exemplary embodiments will be shown in the accompanying drawings and be described in detail in the detailed description. It should be understood, however, that it is not intended to limit the present disclosure to the specific exemplary embodiments but, on the contrary, the present disclosure is to cover all modifications and alternatives falling within the spirit and scope of the present disclosure.

Relational terms such as first, second, and the like may be used for describing various elements, but the elements should not be limited by the terms. These terms are only used to distinguish one element from another. For example, a first component may be named a second component without departing from the scope of the present disclosure, and the second component may also be similarly named the first component. The term "and/or" means any one or a combination of a plurality of related and described items.

When it is mentioned that a certain component is "coupled with" or "connected with" another component, it should be understood that the certain component is directly "coupled with" or "connected with" to the other component or a further component may be disposed therebetween. In contrast, when it is mentioned that a certain component is "directly coupled with" or "directly connected with" another component, it will be understood that a further component is not disposed therebetween.

The terms used in the present disclosure are only used to describe specific exemplary embodiments, and are not intended to limit the present disclosure. The singular expression includes the plural expression unless the context clearly dictates otherwise. In the present disclosure, terms such as 'comprise' or 'have' are intended to designate that a feature, number, step, operation, component, part, or combination thereof described in the specification exists, but it should be understood that the terms do not preclude existence or addition of one or more features, numbers, steps, operations, components, parts, or combinations thereof.

Unless otherwise defined, all terms (including technical and scientific terms) used herein have the same meaning as commonly understood by one of ordinary skill in the art to which this disclosure belongs. Terms that are generally used and have been in dictionaries should be construed as having meanings matched with contextual meanings in the art. In this description, unless defined clearly, terms are not necessarily construed as having formal meanings.

Meanwhile, even if a technology is known prior to the filing date of the present disclosure, it may be included as part of the configuration of the present disclosure when necessary, and will be described herein without obscuring the spirit of the present disclosure. However, in describing the configuration of the present disclosure, a detailed description on matters that can be clearly understood by those skilled in the art as a known technology prior to the filing date of the present disclosure may obscure the purpose of the present disclosure, so excessively detailed description on the known technology will be omitted.

For example, technologies known prior to the filing of the present application may be employed as a technology for detecting, segmenting, and classifying specific organs of the human body and sub-regions of organs by processing medical images, a technology for generating quantitative information by measuring segmented organs or finding areas, and/or the like. At least some of these known technologies may be applied as elemental technologies necessary for practicing the present invention. For example, part of the configuration of US 2013/0004044 entitled "Tissue Phasic Classification Mapping System and Method" may be applied as an elemental technology in order to practice part of the configuration of the present invention.

However, the purpose of the present disclosure is not to claim the rights to these known technologies, and the contents of the known technologies may be included as part of the present disclosure within the scope not departing from the spirit of the present disclosure.

Hereinafter, with reference to the accompanying drawings, preferred exemplary embodiments of the present disclosure will be described in more detail. In order to facilitate overall understanding in the description of the present disclosure, the same reference numerals are used for the same components in the drawings, and redundant descriptions of the same components are omitted.

Figure 1:
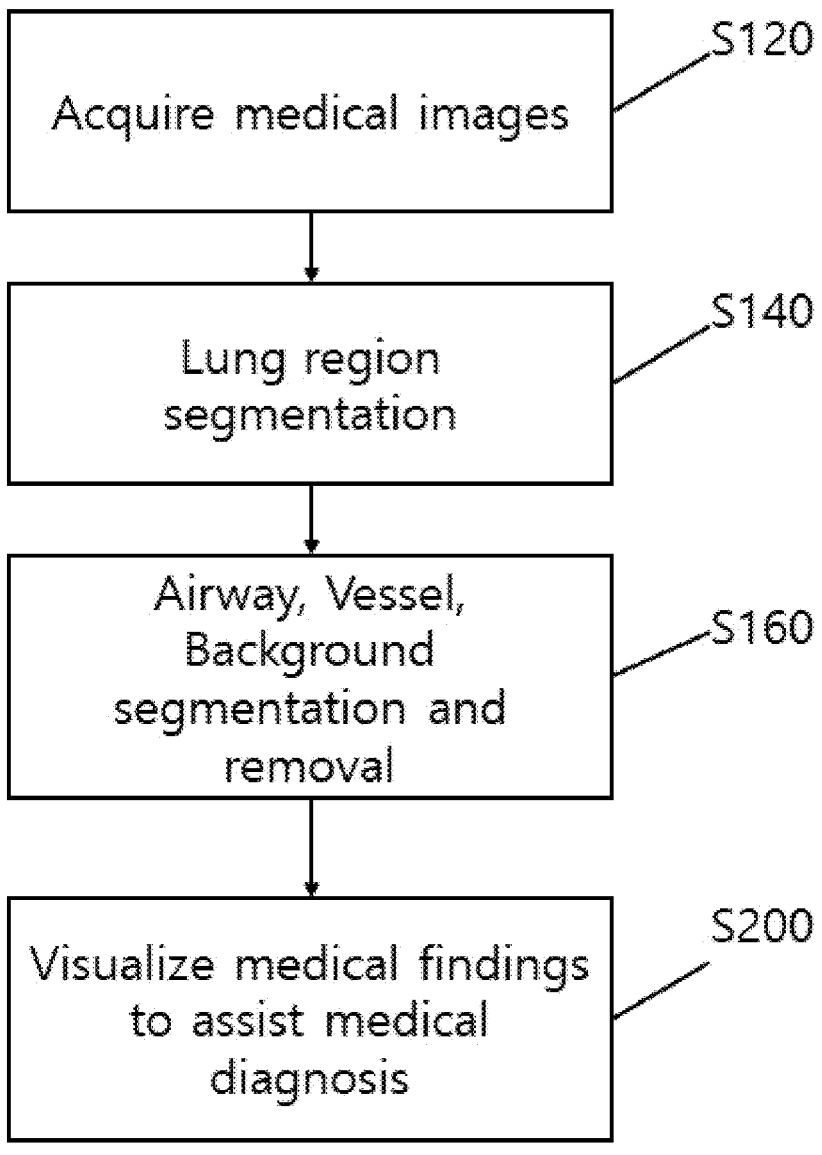
FIG. 1 is an operational flowchart showing the overall process of a visualization method for assisting medical image diagnosis according to an embodiment of the present invention.

FIG. 1 is an operational flowchart showing the overall process of a visualization method for assisting medical image diagnosis according to an embodiment of the present invention.

Referring to FIG. 1, the present invention proposes technology for classifying lung tissue into normal tissue, functional air trapping (fAT), and emphysema.

In the visualization method for assisting medical image diagnosis according to the embodiment of the present invention, medical images including the anatomical structure of the lung region are acquired in step S120.

In the visualization method for assisting medical image diagnosis according to the embodiment of the present invention, a first image data set corresponding to the lung region during inspiration may be generated by segmenting the lung region from a chest CT image acquired during inspiration.

In the visualization method for assisting medical image diagnosis according to the embodiment of the present invention, a second image data set corresponding to the lung region during expiration may be generated by segmenting the lung region from a chest CT image acquired during expiration.

In the visualization method for assisting medical image diagnosis according to the embodiment of the present invention, the first image data set and the second image data set may be deformable-registered.

In the visualization method for assisting medical image diagnosis according to the embodiment of the present invention, the lung region is segmented in step S140.

In the visualization method for assisting medical image diagnosis according to the embodiment of the present invention, the airway, vessels, and/or the background are segmented and removed in step S160.

In the visualization method for assisting medical image diagnosis according to the embodiment of the present invention, different finding regions are classified by applying multiple appropriately designed threshold values to the lung parenchyma in step S200.

Figure 2:
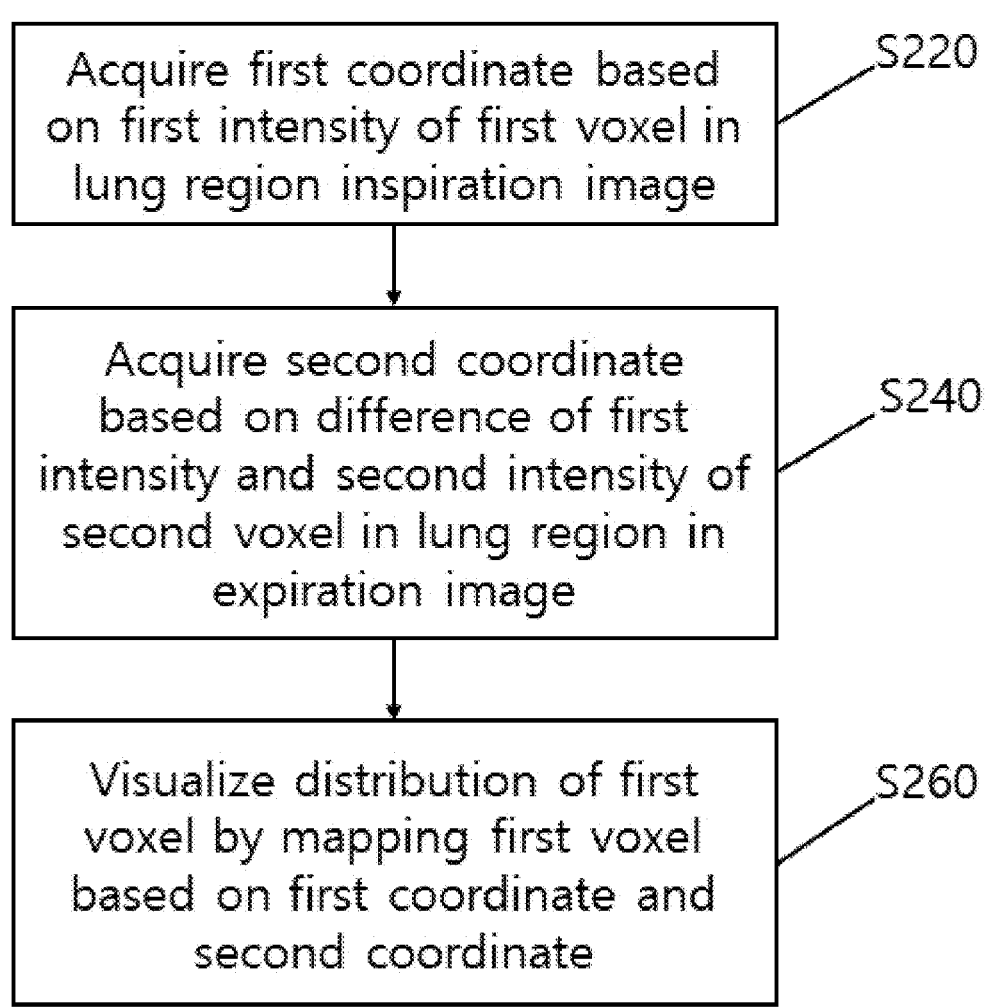
FIG. 2 is an operational flowchart showing in detail part S200 of a visualization method for assisting medical image diagnosis according to an embodiment of the present invention.

FIG. 2 is an operational flowchart showing in detail part S200 of a visualization method for assisting medical image diagnosis according to an embodiment of the present invention.

Referring to FIG. 2, the visualization method for assisting medical image diagnosis according to the embodiment of the present invention includes: step S220 of acquiring the first intensity values of first voxels in the lung region during inspiration, segmented from a chest CT image acquired during inspiration, as the first coordinate values of the first voxels; step S240 of acquiring the differences between the second intensity values of second voxels, registered into the first voxels as voxels in the lung region during expiration segmented from a chest CT image acquired during expiration, and the first intensity values as the second coordinate values of the first voxels; and step S260 of visualizing the distribution of the first voxels by mapping the first voxels based on the first coordinate values and the second coordinate values.

In the visualization method for assisting medical image diagnosis according to the embodiment of the present invention, CT values (the first intensity values) may be acquired as the first coordinate values from the first voxels of the first image data set.

In the visualization method for assisting medical image diagnosis according to the embodiment of the present invention, the differences in CT brightness (|first intensity values–second intensity values|) between the first voxels of the first image data set and the second voxels of the second image data set corresponding to the first voxels of the first image data set may be obtained as the second coordinate values of the first voxels.

The visualization method for assisting medical image diagnosis according to the embodiment of the present invention may further include the step of segmenting the lung region during inspiration into a plurality of sub-regions.

The plurality of sub-regions may include at least one of the right lung, the left lung, the right upper lobe (RUL), the right middle lobe (RML), the right lower lobe, the left upper lobe (LUL), the left lower lobe (LLL), the core, and/or rind regions. The plurality of sub-regions may further include the sub-regions of the lung region that are further subdivided according to functional or anatomical structures.

In this case, step S220 of acquiring the first intensity values as the first coordinate values of the first voxels, step S240 of acquiring the differences between the second intensity values of the second voxels and the first intensity values as the second coordinate values of the first voxels, and step S260 of visualizing the distribution of the first voxels may be performed on at least one of the plurality of sub-regions.

The method shown in FIG. 2 initiates a voxel visualization process performed by mapping first intensity values in an inspiratory image and the differences between second intensity values in an expiratory image and the first intensity values.

FIG. 3 is an operational flowchart showing in detail part S200 of a visualization method for assisting medical image diagnosis according to an embodiment of the present invention.

Redundant descriptions of overlapping configurations between FIGS. 2 and 3, i.e., steps S220, S240, and S260, will be omitted.

Referring to FIG. 3, the visualization method for assisting medical image diagnosis according to the embodiment of the present invention may further include classifying and visualizing a plurality of regions corresponding to different medical findings based on a first threshold value for the first coordinate values and a second threshold value for the second coordinate values.

According to an embodiment of the present invention, criteria for effectively classifying medical finding regions may be presented by setting the first threshold value for the first coordinate values and the second threshold value for the second coordinate values in order to fulfill clinical diagnostic purposes.

The visualization method for assisting medical image diagnosis according to the embodiment of the present invention may further include the step of providing the quantitative analysis results of the distribution of the first voxels in each of the plurality of regions as quantitative assessment information associated with a medical finding corresponding to each of the plurality of regions.

In other words, the distribution of voxels and quantitative analysis information may be visualized for each classified finding region.

The visualization method for assisting medical image diagnosis according to the embodiment of the present invention may further include the step of segmenting the lung region during inspiration into a plurality of sub-regions.

Step S300 of classifying and visualizing a plurality of regions corresponding to different medical findings may be performed on at least one of the plurality of sub-regions.

Figure 4:
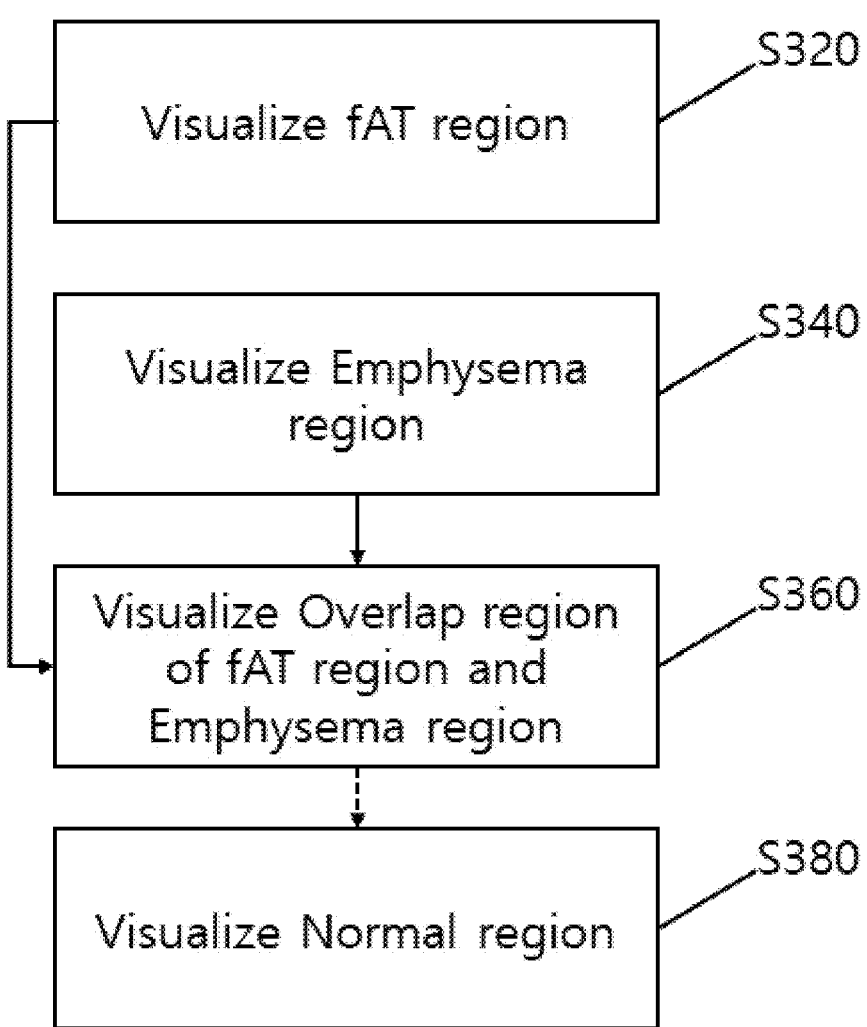
FIG. 4 is an operational flowchart showing in detail part S300 of a visualization method for assisting medical image diagnosis according to an embodiment of the present invention.

FIG. 4 is an operational flowchart showing in detail part S300 of a visualization method for assisting medical image diagnosis according to an embodiment of the present invention.

Referring to FIG. 4, the visualization method for assisting medical image diagnosis according to the embodiment of the present invention may further include step S320 of classifying and visualizing a region, in which the first coordinate values are smaller than the first threshold value and the second coordinate values are smaller than the second threshold value, as a functional air trapping (fAT) region.

The visualization method for assisting medical image diagnosis according to the embodiment of the present invention may further include step S340 of classifying and visualizing a region, in which the first coordinate values are smaller than a third threshold value, as an emphysema region.

The visualization method for assisting medical image diagnosis according to the embodiment of the present invention may further include step S360 of visualizing a region, belonging to both an fAT region and an emphysema region, using a visual element that can distinguish this region from the other regions.

The visualization method for assisting medical image diagnosis according to the embodiment of the present invention may further include step S380 of classifying and visualizing a region, in which the second coordinate values are smaller than the second threshold value and the first coordinate values are equal to or larger than the first threshold value, as a normal region.

The visualization method for assisting medical image diagnosis according to the embodiment of the present invention may further include step S380 of classifying and visualizing a region, in which the second coordinate values are equal to or larger than the second threshold value and the first coordinate values are equal to or larger than the third threshold value, as a normal region.

Each of visualization steps S320, S340, S360, and S380 shown in FIG. 4 may be performed on at least one of a plurality of sub-regions.

Figure 5:
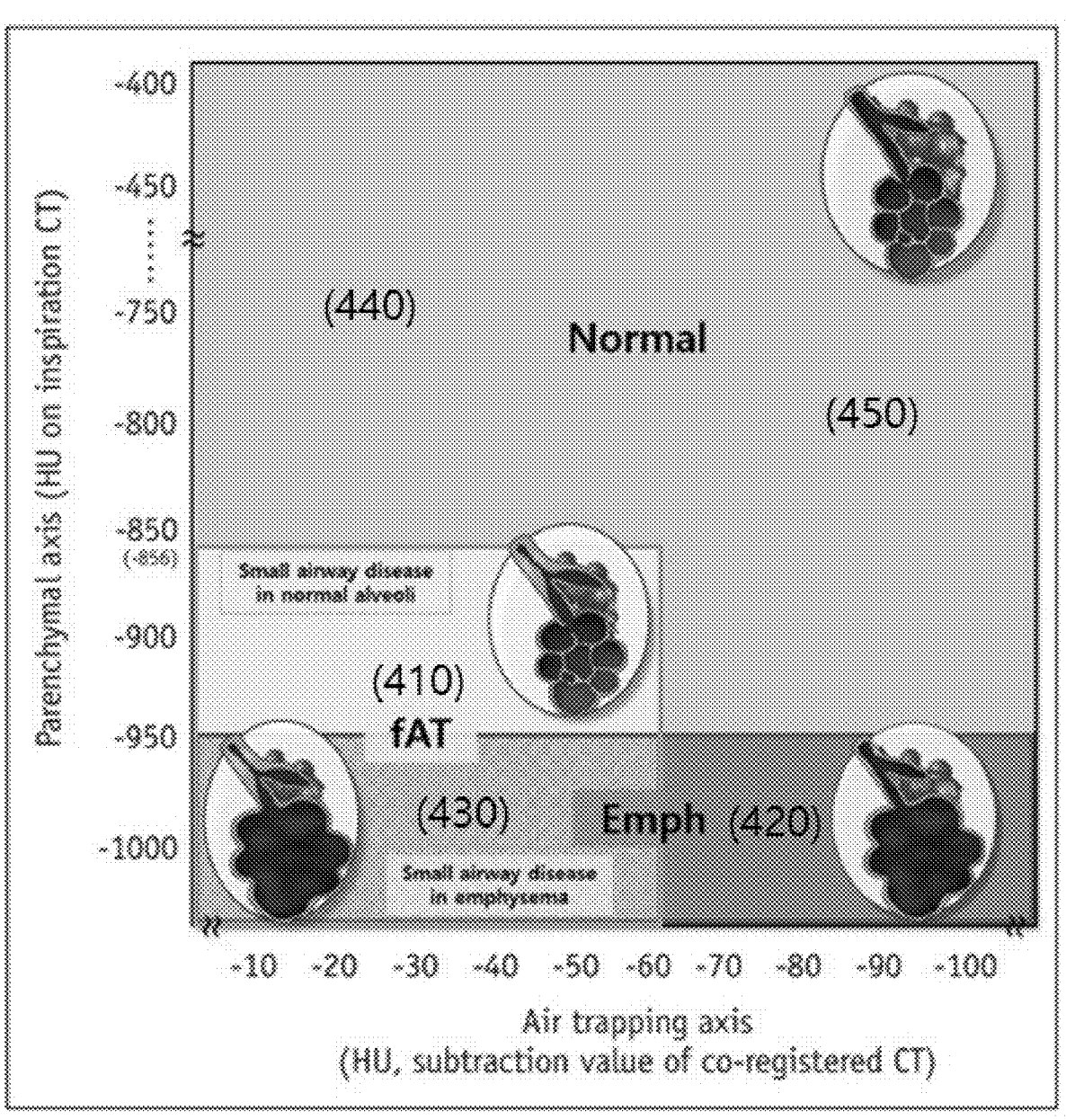
FIG. 5 is a conceptual diagram showing different finding regions visualized in a visualization process for assisting medical image diagnosis according to an embodiment of the present invention.

FIG. 5 is a conceptual diagram showing different finding regions visualized in a visualization process for assisting medical image diagnosis according to an embodiment of the present invention.

Referring to FIGS. 4 and 5, in step S320 of the visualization method for assisting medical image diagnosis according to the embodiment of the present invention, a region in which the first coordinate values are smaller than the first threshold value and the second coordinate values are smaller than the second threshold value may be classified and visualized as an fAT region 410.

In this case, although the first coordinate value is shown as −856 HU (Hounsfield Scale) and the second coordinate value is shown as ±60 HU, the concept of the present invention is not interpreted as being limited to the embodiment of FIG. 5.

In step S340 of the visualization method for assisting medical image diagnosis according to the embodiment of the present invention, a region in which the first coordinate values are smaller than the third threshold value may be classified and visualized as an emphysema region 420.

In this case, although the third coordinate value is shown as −950 HU, the concept of the present invention is not interpreted as being limited to the embodiment of FIG. 5.

In step S360 of the visualization method for assisting medical image diagnosis according to the embodiment of the present invention, an overlap region 430 belonging to both the fAT region 410 and the emphysema region 420 may be visualized using a visual element that can distinguish this region from the other regions.

In step S380 of the visualization method for assisting medical image diagnosis according to the embodiment of the present invention, normal regions 440 and 450 may be visualized by applying a different threshold value for the second coordinate values depending on whether the first coordinate values are smaller than the first threshold value.

In step S380, a region in which the second coordinate values are smaller than the second threshold value and the first coordinate values are equal to or larger than the first threshold value may be classified and visualized as a normal region 440.

Furthermore, in step S380, a region in which the second coordinate values are equal to or larger than the second threshold value and the first coordinate values are equal to or larger than the third threshold value may be classified and visualized as a normal region 450.

Each of the finding regions 410, 420, 430, 440, and 450 shown in FIG. 5 may be performed on at least one of a plurality of sub-regions.

In the embodiment of the present invention shown in FIG. 5, there may be provided a means capable of visualizing and quantifying the results of the quantitative assessment of the respiratory function of the lungs in order to fulfill clinical diagnostic purposes more by setting the horizontal axis to the expiratory-inspiratory subtraction values and the vertical axis to the CT intensity values of an inspiratory image.

In the embodiment of the present invention shown in FIG. 5, there may be provided a means for classifying a region, in which the CT subtraction value of an expiratory-inspiratory image is smaller than a specific threshold value and the inspiratory reference CT value is smaller than a specific threshold value, as an fAT region.

Figure 6:
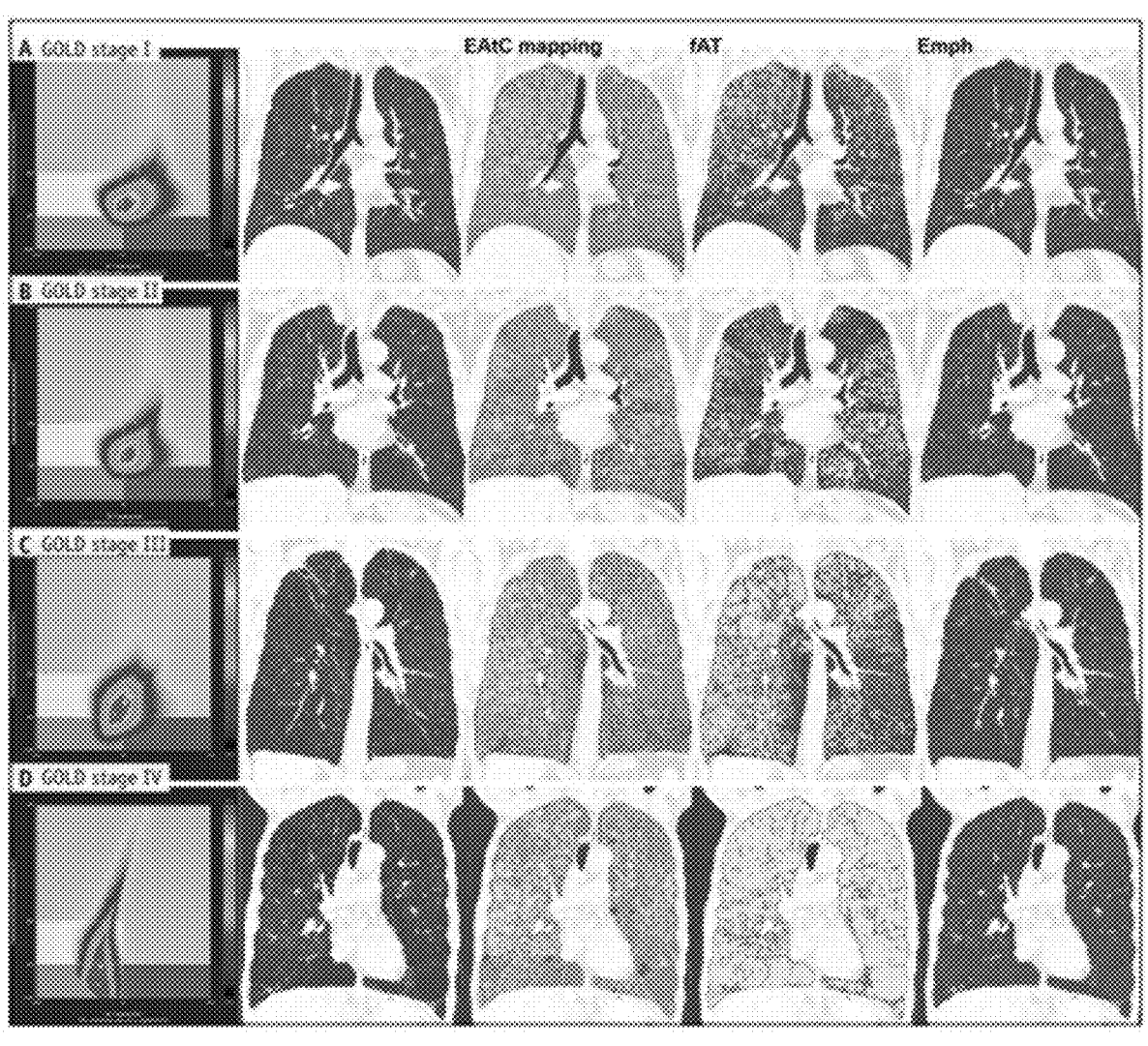
FIG. 6 is a conceptual diagram showing visualization results for assisting medical image diagnosis according to an embodiment of the present invention so that they can be compared with those of a plurality of patients.

FIG. 6 is a conceptual diagram showing visualization results for assisting medical image diagnosis according to an embodiment of the present invention so that they can be compared with those of a plurality of patients.

In FIG. 6, the visualization results of each finding area through emphysema air-trapping composite (EAtC) mapping according to an embodiment of the present invention are shown for each patient so that they can be compared with the results of PFT classified according to Global Initiative for Chronic Obstructive Lung Disease (GOLD) criteria.

In general, a case where the GOLD stage is I is assessed as the least severe, whereas a case where the GOLD stage is IV is assessed as the most severe. Referring to FIG. 6, it can also be seen that the ratio at which voxels in the lung region of a patient having GOLD stage I belong to a normal region is high, most of voxels in the lung region of a patient having GOLD stage IV belong to an fAT region 410, and the ratio at which voxels in the fAT region 410 belong to the overlap region 430 overlapping the emphysema region 420 is also significantly high.

Figure 7:
FIG. 7 is a conceptual diagram showing visualization results for assisting medical image diagnosis according to an embodiment of the present invention.

FIG. 7 is a conceptual diagram showing visualization results for assisting medical image diagnosis according to an embodiment of the present invention.

Referring to FIG. 7, the visualization results according to an embodiment of the present invention may include a first part 510 in which the distribution of voxels in the overall lung region may be visualized in an fAT region, an emphysema region, an overlap region, and a normal region based on a first coordinate axis (expiratory-inspiratory difference values) and a second coordinate axis (inspiration intensity values).

Visualization results according to an embodiment of the present invention may include a second part 520 in which individual voxels are shown on a coronal image of an inspiratory image and a third part 530 in which individual voxels are shown on the coronal image of a matched expiratory-inspiratory image. The individual voxels visualized in the second part 520 and the third part 530 may be shown using different visualization elements in order to be distinguished according to an fAT region, an emphysema region, an overlap region, and a normal region to which the corresponding voxels belong. The visualization elements may be represented using colors, patterns, patterns, figures, and/or the like.

Visualization results according to an embodiment of the present invention may include a fourth part 540 which visualizes the distributions of individual finding regions (an fAT region, an emphysema region, an overlap region, and a normal region) in sub-regions of voxels segmented into the sub-regions including the left and right lungs and five lobes of the lungs, and a fifth part 550 which shows quantitative information for the fourth part 540.

In the fourth part 540 and the fifth part 550, there may be provided a menu capable of indicating whether the voxels currently shown in the first part 510 to the third part 530 belong to the overall region or a specific sub-region. In the fourth part 540 of FIG. 7, all five lobes of the lungs are activated and visualized, indicating that voxels in the overall lung region are visualized in the first part 510 to third part 530 of FIG. 7. In the fifth part 550 of FIG. 7, a "whole lungs" menu may be activated, indicating that voxels of the overall lung region are visualized in the first part 510 to the third part 530 of FIG. 7.

In the fourth part 540 of FIG. 7, the central angle of a fan-shaped region to which each lung lobe corresponds may be determined according to the volume ratio of each lung lobe. In the fourth part 540 of FIG. 7, an emphysema region (excluding an overlap region), an overlap region, and an fAT region (excluding the overlap region) may be visualized from the center based on the distribution ratios or absolute values of voxels. Sub-regions within each fan-shaped region correspond to different finding regions, and the size (radius, or area) of each sub-region may be visualized based on the distribution ratio or absolute values of voxels belonging to each finding region.

Figure 8:
FIG. 8 is a conceptual diagram showing visualization results based on axial images corresponding to coronal images, which are a part of the visualization results of FIG. 7.

FIG. 8 is a conceptual diagram showing visualization results based on axial images corresponding to coronal images, which are a part of the visualization results of FIG. 7.

Referring to FIG. 8, there are shown voxel distribution visualization results based on axial images corresponding to the second part 520 and the third part 530, which are parts of the visualization results of FIG. 7. The visualization results shown in FIG. 8 may include a portion in which individual voxels are shown on an axial image of an inspiratory image and a portion in which individual voxels are shown on an axial image of a matched image, as in the second part 520 and third part 530 of FIG. 7. The individual voxels visualized in FIG. 8 may be shown using different visualization elements so that they can be distinguished according to an fAT region, an emphysema region, an overlap region, and a normal region to which the corresponding voxels belong, as in the second part 520 and third part 530 of FIG. 7.

According to an embodiment of the present invention, the visualization results of FIG. 8 may be visualized in replacement of the second part 520 and third part 530 of FIG. 7 according to a user's selection or a given workflow.

According to another embodiment of the present invention, the visualization results of FIG. 8 may be visualized along with the second part 520 and third part 530 of FIG. 7 or through a separate screen according to a user's selection or a given workflow.

Figure 9:
FIG. 9 is a conceptual diagram showing visualization results based on sagittal images corresponding to coronal images, which are a part of the visualization results of FIG. 7.

FIG. 9 is a conceptual diagram showing visualization results based on sagittal images corresponding to coronal images, which are a part of the visualization results of FIG. 7.

Referring to FIG. 9, there are shown voxel distribution visualization results based on sagittal images corresponding to the second part 520 and the third part 530, which are parts of the visualization results of FIG. 7. The visualization results shown in FIG. 9 may include a portion in which individual voxels are shown on a sagittal image of an inspiratory image and a portion in which individual voxels are shown on a matched image, as in the second part 520 and third part 530 of FIG. 7. The individual voxels visualized in FIG. 9 may be shown using different visualization elements so that they can be distinguished according to an fAT region, an emphysema region, an overlap region, and a normal region to which the corresponding voxels belong, as in the second part 520 and third part 530 of FIG. 7.

According to an embodiment of the present invention, the visualization results of FIG. 9 may be visualized in replacement of the second part 520 and third part 530 of FIG. 7 according to a user's selection or a given workflow.

According to another embodiment of the present invention, the visualization results of FIG. 9 may be visualized along with the second part 520 and third part 530 of FIG. 7 or through a separate screen according to a user's selection or a given workflow.

Figure 10:
FIG. 10 is a conceptual diagram showing in detail the quantitative assessment results of the fifth part 550, which are a part of the visualization results of FIG. 7.

FIG. 10 is a conceptual diagram showing in detail the quantitative assessment results of the fifth part 550, which are a part of the visualization results of FIG. 7.

Referring to FIG. 10, there is shown diagnostic assistance information for the lung region that is generated by quantifying the distributions of individual voxels as a result of applying a threshold value to the CT subtraction values of expiratory-inspiratory images of the individual voxels and an inspiratory reference CT value.

In FIG. 10, there is shown the area occupancy ratio of each finding region to a reference region (the overall region of the lung region or a sub-region of the lung region). In contrast, in another embodiment of the present invention, the volume occupancy ratio of each finding region to each reference region may be represented by an absolute value. In this case, a value obtained by summing the volumes of voxels belonging to each finding region is shown, and the unit thereof may be cc.

According to the embodiments of the present invention shown in FIGS. 1 to 10, there is shown a workflow in which diagnostic assistance information is generated by classifying individual voxels within images based on threshold values after the non-rigid registration of expiratory-inspiratory lung images and then quantifying the distributions of voxels for respective finding regions based on threshold values.

Figure 11:
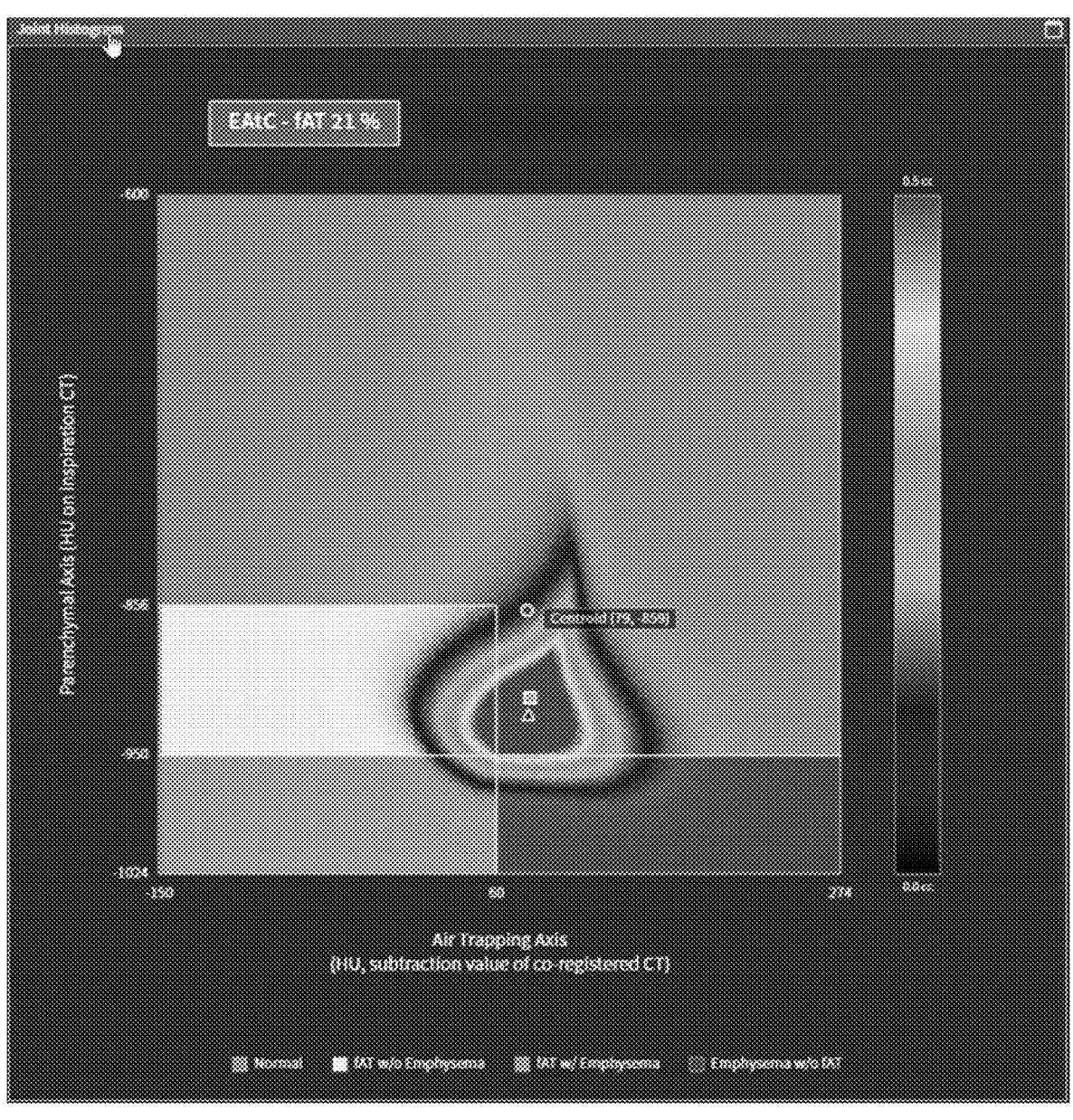
FIG. 11 is a conceptual view showing the distributions of voxels visualized on different finding regions and the centroid of the distributions of voxels as another embodiment of the visualization results of FIG. 7.

FIG. 11 is a conceptual view showing the distributions of voxels visualized on different finding regions and the centroid of the distributions of voxels as another embodiment of the visualization results of FIG. 7.

Referring to FIG. 11, the distributions of voxels within a reference region (the overall lung region or a sub-region) are mapped to different finding regions and visualized. The centroid of the distributions of voxels within the reference area may be determined and visualized by the distributions of voxels within the reference area, regardless of the finding areas.

Figure 12:
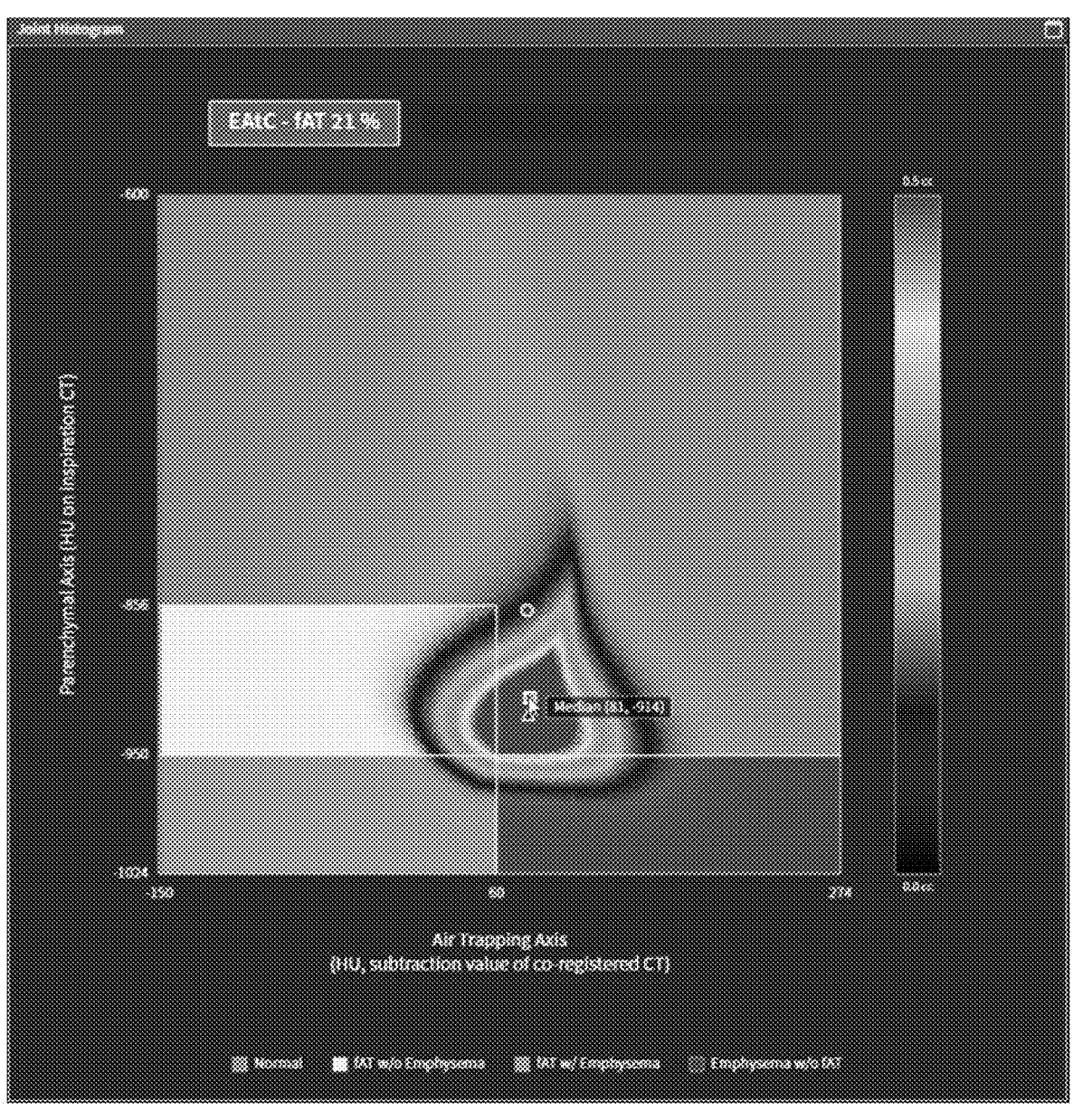
FIG. 12 is a conceptual view showing the distributions of voxels visualized on different finding regions and the median of the distributions of voxels as another embodiment of the visualization results of FIG. 7.

FIG. 12 is a conceptual view showing the distributions of voxels visualized on different finding regions and the median of the distributions of voxels as another embodiment of the visualization results of FIG. 7.

Referring to FIG. 12, the distributions of voxels within a reference region (the overall lung region or a sub-region) are mapped to different finding regions and visualized, as in FIG. 11. The median of the distributions of voxels within the reference area may be determined and visualized by the distributions of voxels within the reference area, regardless of the finding areas.

Figure 13:
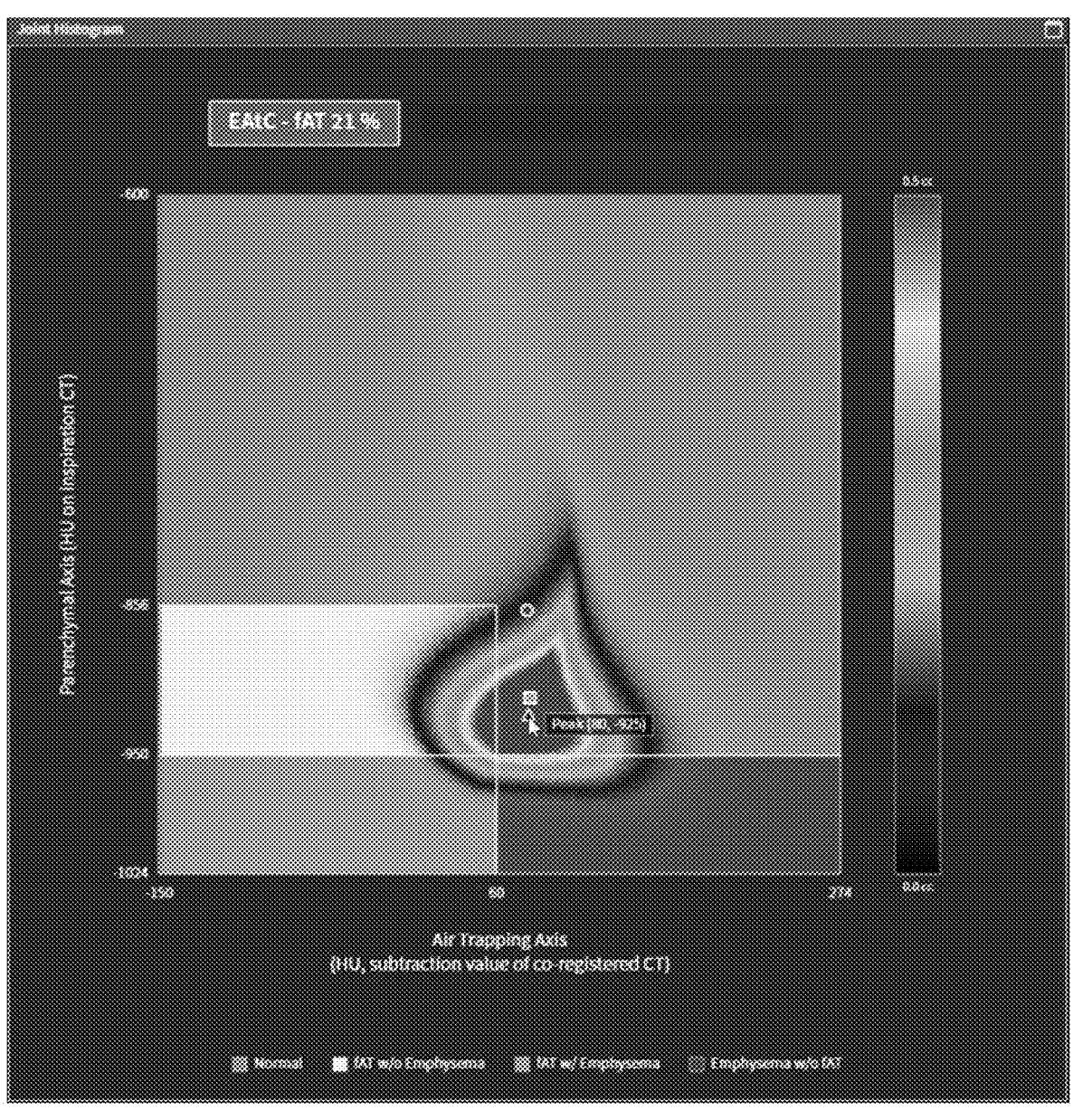
FIG. 13 is a conceptual view showing the distributions of voxels visualized on different finding regions and the peak of the distributions of voxels as another embodiment of the visualization results of FIG. 7.

FIG. 13 is a conceptual view showing the distributions of voxels visualized on different finding regions and the peak of the distributions of voxels as another embodiment of the visualization results of FIG. 7.

Referring to FIG. 12, the distributions of voxels within a reference region (the overall lung region or a sub-region of the lung region) are mapped to different finding regions and visualized, as in FIGS. 11 and 12. The peak of the distributions of voxels within the reference area may be determined and visualized by the distributions of voxels within the reference area, regardless of the finding areas.

In the embodiments of FIGS. 11 to 13, the representative value or location of the distributions of voxels such as the centroid, the median, or the peak may be selectively shown according to a user's selection or a given workflow.

FIGS. 14 to 21 are conceptual views showing visualization results for assisting medical image diagnosis for a reference region (the overall lung region or a sub-region) according to still another embodiment of the present invention.

Like FIG. 7, FIGS. 14 to 21 include: a first part 510 in which voxels within a reference region are classified and mapped into finding regions; a second part 520 in which voxels are voxels are shown on an inspiratory coronal image using visualization elements distinguishable for respective finding regions to which the voxels belong; a third part 530 in which voxels are voxels are shown on a matched coronal image using visualization elements distinguishable for respective finding regions to which the voxels belong; a fourth part 540 which shows information about the reference region to which the voxels shown in the first part 510 to third part 530 belong, and quantitative information for the finding regions of the voxels within the reference region in the form of a graph; and a fifth part 550 which represents the quantitative information corresponding to the fourth part 540 in the form of a table.

FIG. 14 is a conceptual view showing visualization results for assisting medical image diagnosis for the overall lung region according to still another embodiment of the present invention.

The first part 510 to third part 530 of FIG. 14 may visualize the distributions of voxels using the overall lung region as a reference region. The fourth part 540 may indicate that the voxels visualized in the first to third parts 510 to 530 are visualized using the overall lung region as a reference region by activating and visualizing an overall sub-region. The fifth part 550 may indicate that the voxels visualized in the first part 510 to the third part 530 are visualized using the overall lung region as a reference region by means of an activated line in a table.

Figure 15:
FIG. 15 is a conceptual view showing visualization results for assisting medical image diagnosis for the right lung region corresponding to FIG. 14.

FIG. 15 is a conceptual view showing visualization results for assisting medical image diagnosis for the right lung region corresponding to FIG. 14.

The first part 510 to third part 530 of FIG. 15 may visualize the distribution of voxels using the right lung region as a reference region. The fourth part 540 may indicate that the voxels visualized in the first part 510 to the third part 530 are visualized using the right lung region as the reference region by activating the right lung region among the sub-regions. The fifth part 550 may indicate that voxels visualized in the first part 510 to the third part 530 are visualized using the right lung region as the reference region by using an activated line in a table.

FIG. 16 is a conceptual view showing visualization results for assisting in medical image diagnosis for the left lung region corresponding to FIG. 14.

The first part 510 to third part 530 of FIG. 15 may visualize the distribution of voxels using the left lung region as a reference region. The fourth part 540 may indicate that the voxels visualized in the first part 510 to the third part 530 are visualized using the left lung region as a reference region by activating the left lung region among the sub-regions. The fifth part 550 may indicate that the voxels visualized in the first part 510 to the third part 530 are visualized using the left lung region as a reference region by means of an activated line in a table.

Figure 17:
FIG. 17 is a conceptual view showing visualization results for assisting medical image diagnosis for the right upper lobe (RUL) region corresponding to FIGS. 14 and 15.

FIG. 17 is a conceptual view showing visualization results for assisting medical image diagnosis for the right upper lobe (RUL) region corresponding to FIGS. 14 and 15.

The fourth part 540 of FIG. 17 activates and visualizes the upper right lobe region among the lower regions, and the fifth part 550 may indicate that the voxels visualized in the first part 510 to the third part 530 of FIG. 17 are visualized using the upper right lobe region as a reference region by means of an activated line in a table.

Figure 18:
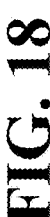
FIG. 18 is a conceptual view showing visualization results for assisting medical image diagnosis for the right middle lobe (RML) region corresponding to FIGS. 14 and 15.

FIG. 18 is a conceptual view showing visualization results for assisting medical image diagnosis for the right middle lobe (RML) region corresponding to FIGS. 14 and 15.

The fourth part 540 of FIG. 18 activates and visualizes the right middle lobe region among the lower regions, and the fifth part 550 may indicate that the voxels visualized in the first part 510 to third part of FIG. 18 are visualized using the right middle lobe region as a reference region by means of an activated line in a table.

Figure 19:
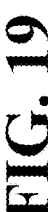
FIG. 19 is a conceptual view showing visualization results for assisting medical image diagnosis for the right lower lobe (RLL) region corresponding to FIGS. 14 and 15.

FIG. 19 is a conceptual view showing visualization results for assisting medical image diagnosis for the right lower lobe (RLL) region corresponding to FIGS. 14 and 15.

The fourth part 540 of FIG. 19 activates and visualizes the right lower lobe region among the lower regions, and the fifth part 550 may indicate that the voxels visualized in the first part 510 to third part 530 of FIG. 19 are visualized using the right lower lobe region as a reference region by means of an activated line in a table.

FIG. 20 is a conceptual view showing visualization results for assisting medical image diagnosis for the left upper lobe (LUL) region corresponding to FIGS. 14 and 16.

The fourth part 540 of FIG. 20 activates and visualizes the upper left lobe region among the lower regions, and the fifth part 550 may indicate that the voxels visualized in the first part 510 to third part 530 of FIG. 20 are visualized using the upper left lobe region as a reference region by means of an activated line in a table.

FIG. 21 is a conceptual view showing visualization results for assisting medical image diagnosis for the left lower lobe (LLL) region corresponding to FIGS. 14 and 16.

The fourth part 540 of FIG. 21 activates and visualizes the lower left lobe region among the lower regions, and the fifth part 550 may indicate that the voxels visualized in the first part 510 to third part 530 of FIG. 21 are visualized using the lower left lobe region as a reference region by means of an activated line in a table.

According to an embodiment of the present invention, there may be proposed and visualized criteria capable of quantitatively assessing the severity of a patient in order to diagnose COPD.

According to an embodiment of the present invention, there may be provided improved criteria capable of identifying and visualizing an fAT region and an emphysema region, which are essential for the quantitative analysis of COPD.

According to an embodiment of the present invention, there may be provided intuitive information that can assist a medical profession in diagnosis by identifying and visualizing an fAT region and an emphysema region, which are essential for the quantitative analysis of COPD.

According to an embodiment of the present invention, there may be provided an analysis method having improved clinical accuracy because the quantification results of a region diagnosed as a dysfunctional region have a higher correlation with the results of PFT than those of the prior art.

According to an embodiment of the present invention, emphysema, an fAT region, and a normal region may be effectively identified, so that, particularly, a normal region can be prevented from being unnecessarily classified as a disease region, and accurate quantification indices can be acquired.

According to an embodiment of the present invention, quantification indices significantly closer to the results of clinical PFT may be acquired by acknowledging the presence of a functionally overlapping region without unduly classifying the region as an emphysema region or an fAT region.

FIG. 22 is a conceptual diagram showing an example of a generalized medical image analysis apparatus, a visualization apparatus for assisting medical image diagnosis, or a computing system capable of performing at least part of the processes of FIGS. 1 to 21.

At least part of the processes of the medical image analysis method, the visualization method for assisting medical image diagnosis, and/or the method for the quantitative assessment of medical images for the diagnosis of COPD according to the embodiment of the present invention may be performed in the computing system 1000 of FIG. 22.

As shown in FIG. 22, the computing system 1000 according to an exemplary embodiment of the present disclosure may be configured to include a processor 1100, a memory 1200, a communication interface 1300, a storage device 1400, an input interface 1500, an output interface 1600, and a bus 1700.

The computing system 1000 according to an exemplary embodiment of the present disclosure may include the at least one processor 1100 and the memory 1200 storing instructions instructing the at least one processor 1100 to perform at least one step. At least some steps of the method according to exemplary embodiments of the present disclosure may be performed by the at least one processor 1100 loading the instructions from the memory 1200 and executing them.

The processor 1100 may mean a central processing unit (CPU), a graphics processing unit (GPU), or a dedicated processor on which the methods according to exemplary embodiments of the present disclosure are performed.

Each of the memory 1200 and the storage device 1400 may include at least one of a volatile storage medium and a non-volatile storage medium. For example, the memory 1200 may include at least one of a read only memory (ROM) and a random access memory (RAM).

In addition, the computing system 1000 may include the communication interface 1300 that performs communication through a wireless network.

In addition, the computing system 1000 may include the storage 1400, input user interface 1500, and output user interface 1600.

In addition, the respective components included in the computing system 1000 may be connected by the bus 1700 to communicate with each other.

For example, the computing system 1000 of the present disclosure may be a desktop computer, a laptop computer, a notebook, a smart phone, a tablet PC, a mobile phone, a smart watch, a smart glass, e-book reader, a portable multimedia player (PMP), a portable gaming device, a navigation device, a digital camera, a digital multimedia broadcasting (DMB) player, a digital audio recorder, a digital audio player, a digital video recorder, a digital video player, a personal digital assistant (PDA), and the like having communication capability.

A visualization apparatus for assisting medical image diagnosis according to an embodiment of the present invention includes memory 1200 configured to store at least one instruction, and a processor 1100 may configured to execute the at least one instruction. The processor 1100 may execute the at least one instruction to acquire the first intensity values of first voxels in the lung region during inspiration, segmented from a chest CT image acquired during inspiration, as the first coordinate values of the first voxels (see step S220), to acquire the differences between the second intensity values of second voxels, registered into the first voxels as voxels in the lung region during expiration segmented from a chest CT image acquired during expiration, and the first intensity values as the second coordinate values of the first voxels (see step S240), and to visualize the distribution of the first voxels by mapping the first voxels based on the first coordinate values and the second coordinate values (see step S260).

The processor 1100 may execute the at least one instruction to classify and visualize a plurality of regions corresponding to different medical findings based on a first threshold value for the first coordinate values and a second threshold value for the second coordinate values (see step S300).

The processor 1100 may execute the at least one instruction to provide the quantitative analysis results of the distribution of the first voxels in each of the plurality of regions as quantitative assessment information associated with a medical finding corresponding to each of the plurality of regions.

The processor 1100 may execute the at least one instruction to classify and visualize a region, in which the first coordinate values are smaller than a first threshold value and the second coordinate values are smaller than a second threshold value, as an fAT region (see step S320).

The processor 1100 may execute the at least one instruction to classify and visualize a region, in which the first coordinate values are smaller than a third threshold value, as an emphysema region (see step S340).

The processor 1100 may execute the at least one instruction to visualize a region, belonging to both the fAT region and the emphysema region, using a visual element that can distinguish this region from the other regions (see step S360).

The processor 1100 may execute the at least one instruction to classify and visualize a region, in which the second coordinate values are smaller than the second threshold value and the first coordinate values are equal to or larger than the first threshold value, as a normal region (see step S380).

The processor 1100 may execute the at least one instruction to classify and visualize a region, in which the second coordinate values are equal to or larger than the second threshold value and the first coordinate values are equal to or larger than the third threshold value, as a normal region (see step S380).

The processor 1100 may execute the at least one instruction to segment the lung region during inspiration into a plurality of sub-regions.

The processor 1100 may execute the at least one instruction to acquire the first intensity values as the first coordinate values of the first voxels for at least one of the plurality of sub-regions.

The processor 1100 may execute the at least one instruction to acquire the differences between the second intensity values of second voxels and the first intensity values as the second coordinate values of the first voxels for at least one of the plurality of sub-regions.

The processor 1100 may execute the at least one instruction to visualize the distribution of the first voxels for at least one of the plurality of sub-regions.

The processor 1100 may execute the at least one instruction to classify and visualize a plurality of regions corresponding to different medical findings for at least one of the plurality of sub-regions.

The operations of the method according to the exemplary embodiment of the present disclosure can be implemented as a computer readable program or code in a computer readable recording medium. The computer readable recording medium may include all kinds of recording apparatus for storing data which can be read by a computer system. Furthermore, the computer readable recording medium may store and execute programs or codes which can be distributed in computer systems connected through a network and read through computers in a distributed manner.

The computer readable recording medium may include a hardware apparatus which is specifically configured to store and execute a program command, such as a ROM, RAM or flash memory. The program command may include not only machine language codes created by a compiler, but also high-level language codes which can be executed by a computer using an interpreter.

Although some aspects of the present disclosure have been described in the context of the apparatus, the aspects may indicate the corresponding descriptions according to the method, and the blocks or apparatus may correspond to the steps of the method or the features of the steps. Similarly, the aspects described in the context of the method may be expressed as the features of the corresponding blocks or items or the corresponding apparatus. Some or all of the steps of the method may be executed by (or using) a hardware apparatus such as a microprocessor, a programmable computer or an electronic circuit. In some embodiments, one or more of the most important steps of the method may be executed by such an apparatus.

In some exemplary embodiments, a programmable logic device such as a field-programmable gate array may be used to perform some or all of functions of the methods described herein. In some exemplary embodiments, the field-programmable gate array may be operated with a microprocessor to perform one of the methods described herein. In general, the methods are preferably performed by a certain hardware device.

The description of the disclosure is merely exemplary in nature and, thus, variations that do not depart from the substance of the disclosure are intended to be within the scope of the disclosure. Such variations are not to be regarded as a departure from the spirit and scope of the disclosure. Thus, it will be understood by those of ordinary skill in the art that various changes in form and details may be made without departing from the spirit and scope as defined by the following claims.

What is claimed is:

1. A visualization method for assisting medical image diagnosis, the visualization method comprising:
acquiring first intensity values of first voxels in a lung region during inspiration, segmented from a chest computed tomography (CT) image acquired during inspiration, as first coordinate values of the first voxels;
acquiring differences between second intensity values of second voxels, registered into the first voxels as voxels in the lung region during expiration segmented from a chest CT image acquired during expiration, and the first intensity values as second coordinate values of the first voxels; and
visualizing a distribution of the first voxels by mapping the first voxels based on the first coordinate values and the second coordinate values.

2. The visualization method of claim 1, further comprising classifying and visualizing a plurality of regions corresponding to different medical findings based on a first threshold value for the first coordinate values and a second threshold value for the second coordinate values.

3. The visualization method of claim 2, further comprising providing quantitative analysis results of a distribution of the first voxels in each of the plurality of regions as quantitative assessment information associated with a medical finding corresponding to each of the plurality of regions.

4. The visualization method of claim 2, further comprising further comprising segmenting the lung region during inspiration into a plurality of sub-regions;
wherein the classifying and visualizing is performed on at least one of the plurality of sub-regions.

5. The visualization method of claim 1, further comprising classifying and visualizing a region, in which the first coordinate values are smaller than a first threshold value and the second coordinate values are smaller than the second threshold value, as a functional air trapping (fAT) region.

6. The visualization method of claim 5, further comprising classifying and visualizing a region, in which the first coordinate values are smaller than a third threshold value, as an emphysema region.

7. The visualization method of claim 6, further comprising visualizing a region, belonging to both the fAT region and the emphysema region, using a visual element that can distinguish this region from remaining regions.

8. The visualization method of claim 6, further comprising classifying and visualizing a region, in which the second coordinate values are equal to or larger than the second threshold value and the first coordinate values are equal to or larger than the third threshold value, as a normal region.

9. The visualization method of claim 5, further comprising classifying and visualizing a region, in which the second coordinate values are smaller than the second threshold value and the first coordinate values are equal to or larger than the first threshold value, as a normal region.

10. The visualization method of claim 1, further comprising segmenting the lung region during inspiration into a plurality of sub-regions;
wherein the acquiring the first intensity values, the acquiring the differences, and the visualizing are performed on at least one of the plurality of sub-regions.

11. A visualization apparatus for assisting medical image diagnosis, the visualization apparatus comprising:
memory configured to store at least one instruction; and
a processor configured to execute the at least one instruction;
wherein the processor executes the at least one instruction to:
acquire first intensity values of first voxels in a lung region during inspiration, segmented from a chest computed tomography (CT) image acquired during inspiration, as first coordinate values of the first voxels;
acquire differences between second intensity values of second voxels, registered into the first voxels as voxels in the lung region during expiration segmented from a chest CT image acquired during expiration, and the first intensity values as second coordinate values of the first voxels; and
visualize a distribution of the first voxels by mapping the first voxels based on the first coordinate values and the second coordinate values.

12. The visualization apparatus of claim 11, wherein the processor executes the at least one instruction to classify and visualize a plurality of regions corresponding to different medical findings based on a first threshold value for the first coordinate values and a second threshold value for the second coordinate values.

13. The visualization apparatus of claim 12, wherein the processor executes the at least one instruction to provide quantitative analysis results of a distribution of the first voxels in each of the plurality of regions as quantitative assessment information associated with a medical finding corresponding to each of the plurality of regions.

14. The visualization apparatus of claim 12, wherein the processor executes the at least one instruction to:
segment the lung region during inspiration into a plurality of sub-regions; and
classify and visualize a plurality of regions corresponding to different medical findings for at least one of the plurality of sub-regions.

15. The visualization apparatus of claim 11, wherein the processor executes the at least one instruction to classify and visualize a region, in which the first coordinate values are smaller than a first threshold value and the second coordinate values are smaller than a second threshold value, as a functional air trapping (fAT) region.

16. The visualization apparatus of claim 15, wherein the processor executes the at least one instruction to classify and visualize a region, in which the first coordinate values are smaller than a third threshold value, as an emphysema region.

17. The visualization apparatus of claim 16, wherein the processor executes the at least one instruction to visualize a region, belonging to both the fAT region and the emphysema region, using a visual element that can distinguish this region from remaining regions.

18. The visualization apparatus of claim 16, wherein the processor executes the at least one instruction to classify and visualize a region, in which the second coordinate values are equal to or larger than the second threshold value and the first coordinate values are equal to or larger than the third threshold value, as a normal region.

19. The visualization apparatus of claim 15, wherein the processor executes the at least one instruction to classify and visualize a region, in which the second coordinate values are smaller than the second threshold value and the first coordinate values are equal to or larger than the first threshold value, as a normal region.

20. The visualization apparatus of claim 11, wherein the processor executes the at least one instruction to:

segment the lung region during inspiration into a plurality of sub-regions;

acquire the first intensity values as first coordinate values of the first voxels for at least one of the plurality of sub-regions;

acquire differences between second intensity values of second voxels and the first intensity values as second coordinate values of the first voxels for at least one of the plurality of sub-regions; and visualize a distribution of the first voxels for at least one of the plurality of sub-regions.

\* \* \* \* \*